United States Patent
Eshel et al.

[11] Patent Number: 5,916,195
[45] Date of Patent: Jun. 29, 1999

[54] INTERNAL CATHETER

[75] Inventors: Uzi Eshel, Herzelia; Jacob Lazarovitz, Hod Hasharon, both of Israel

[73] Assignee: Argomed Ltd., Herzelia, Israel

[21] Appl. No.: 09/018,664

[22] Filed: Feb. 4, 1998

[51] Int. Cl.⁶ .................................................. A61M 29/00
[52] U.S. Cl. ................................ 604/96; 604/264; 623/12
[58] Field of Search ............................ 604/96, 101, 264, 604/53; 606/195; 623/12

[56] References Cited

U.S. PATENT DOCUMENTS

| | | | |
|---|---|---|---|
| 3,811,450 | 5/1974 | Lord | 604/96 |
| 5,718,680 | 2/1998 | Kraus et al. | 604/53 |

*Primary Examiner*—Wynn Wood Coggins
*Assistant Examiner*—N. Kent Gring
*Attorney, Agent, or Firm*—Mark M. Friedman

[57] ABSTRACT

A catheter for insertion into a patient's urethra is provided, comprising: (a) first and second tubular members having such a diameter for enabling drainage of physiological fluids therethrough, the first and second tubular members being interconnected by means of a connecting tube of substantially smaller diameter; (b) an inflatable balloon attached to the second tubular member, the inflatable balloon being in fluid communication with the connecting tube. The inflatable balloon is inserted to the patient's urinary bladder so as to locate the second tubular member substantially within the patient's prostatic urethra such that the connecting tube is held by the patient's sphincter. Further according to the present invention there is provided a guiding element for insertion through the catheter, including: (a) a substantially elongated tubular member having a hollow, the elongated tubular member having a closed end for insertion through the patient's urethra and an open end for connection to an external inflating element; (b) an inflatable balloon attached to the elongated tubular member, the inflatable balloon being in fluid communication with the hollow of the tubular element, the inflatable balloon for inflation against the catheter so as to effectively fix the guiding element to the catheter.

7 Claims, 2 Drawing Sheets

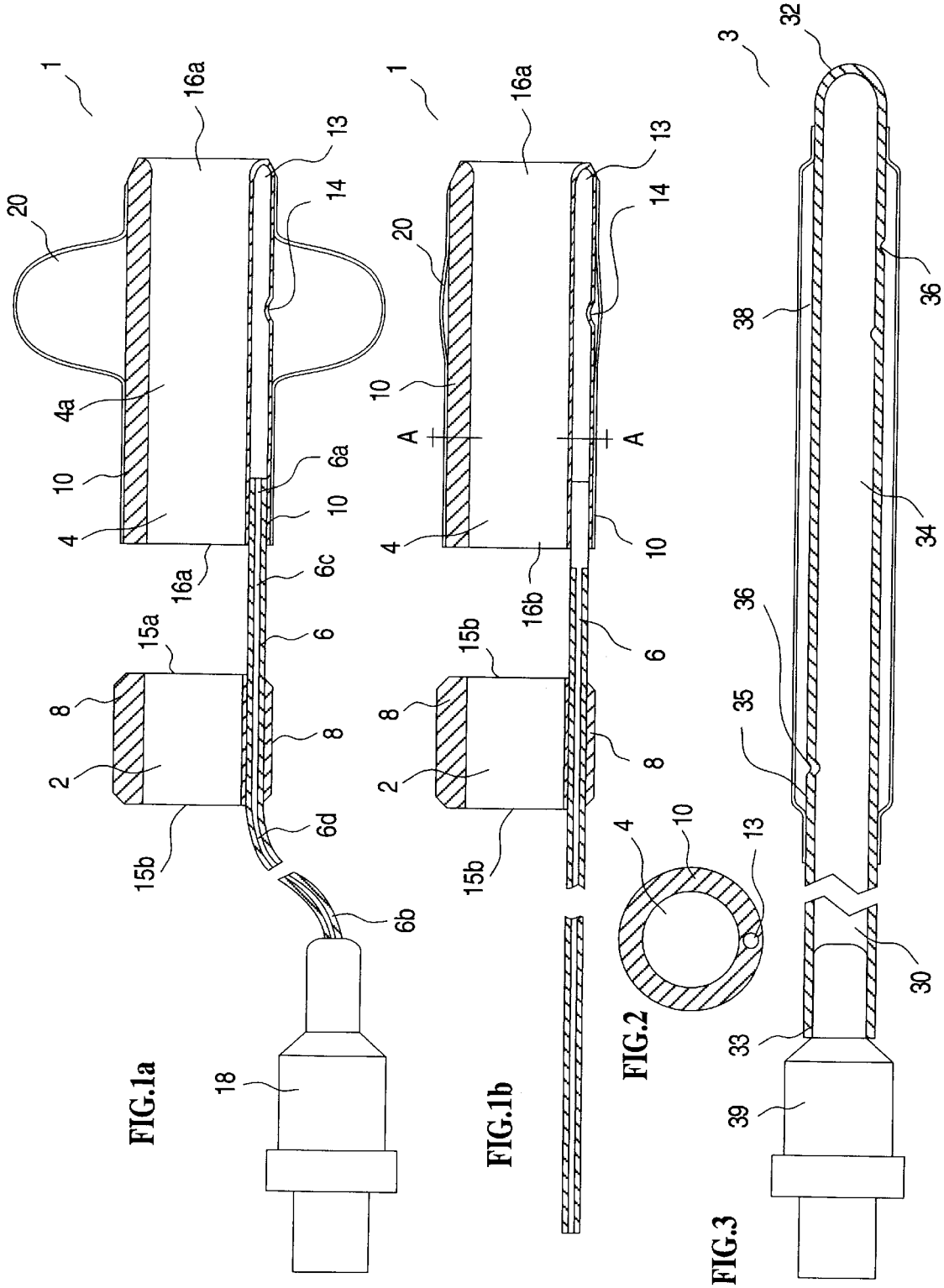

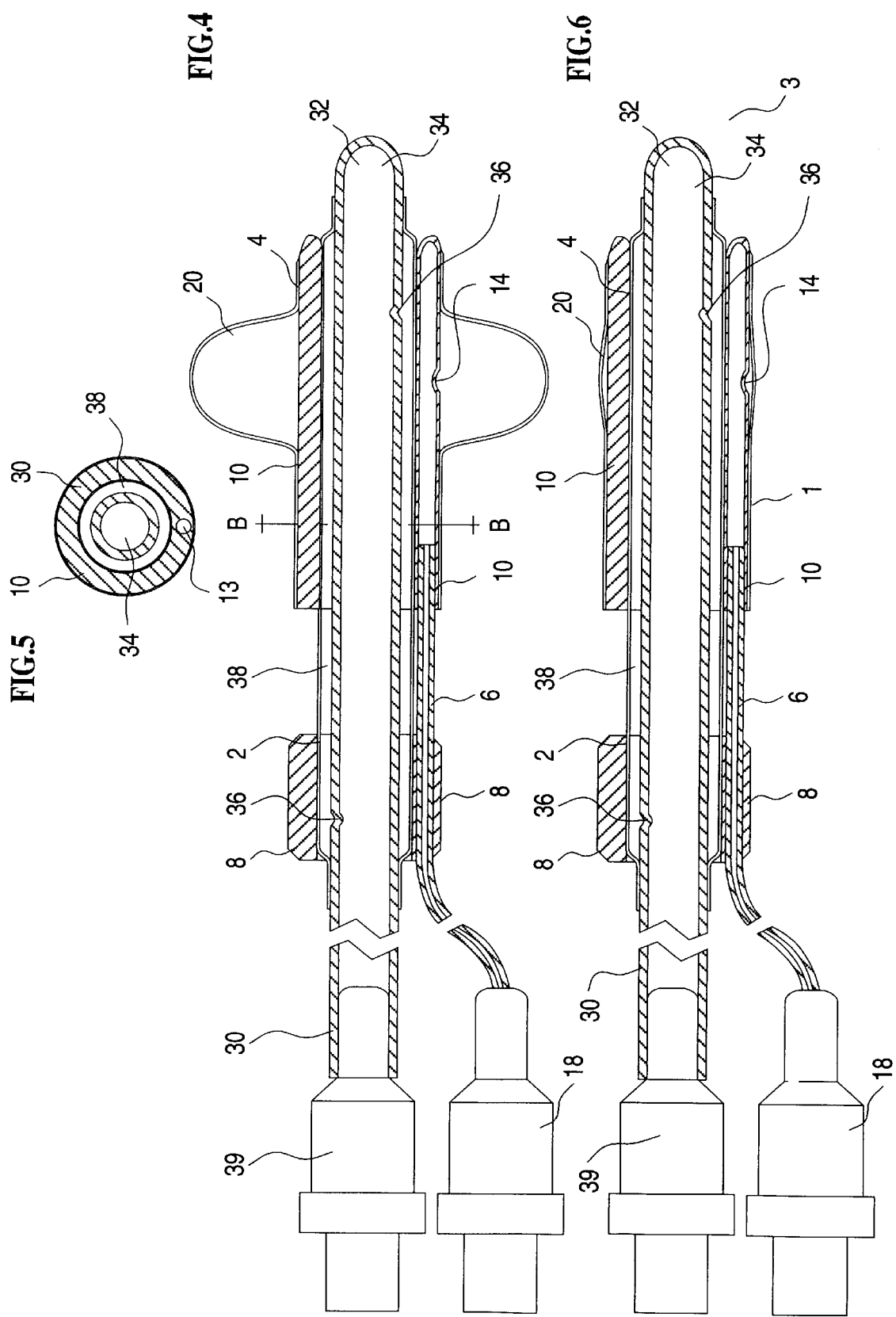

INTERNAL CATHETER

FIELD AND BACKGROUND OF THE INVENTION

The present invention relates to an internal catheter for insertion into the urethra of a patient and, more particularly to a catheter specifically adapted for treating obstruction of the prostatic urethra. Such a catheter may be used for drainage of fluids and tissue particles through the patient's prostatic urethra following a non-surgical medical procedure such as thermal treatment of the prostate, wherein a long-term indwelling catheter is needed.

Benign prostate hyperplasia (BPH) is currently treated by using surgical procedures such as trans urethral resection of the prostate (TURP) or non-surgical procedures such as thermal treatment of the prostate. Temporary blockage of the prostatic urethra usually takes place following such treatments due to extensive swelling and edema formation.

Various attempts have been made to provide internal catheters or stents for insertion into the patient's prostatic urethra for enabling effective drainage of fluids and tissue particles therethrough.

Examples of such internal catheters and stents are disclosed in U.S. Pat. Nos. 3,811,450; 5,176,626; and 5,514,178.

However, none of the prior art devices provides an internal catheter having first and second cylindrical members interconnected by means of a tube, the tube for inflating a balloon located at the end of the catheter, the balloon for appropriately locating the catheter at the prostatic urethra.

Further, none of the prior art devices provide a guiding element including an inflatable balloon for introducing the catheter to the patient's urethra.

SUMMARY OF THE INVENTION

According to the present invention there is provided a catheter for insertion into a patient's urethra, comprising: (a) first and second tubular members having such a diameter for enabling drainage of physiological fluids therethrough, each of the first and second tubular members having a wall of a specific thickness, the first and second tubular members being interconnected by means of a connecting tube of substantially smaller diameter; (b) an inflatable balloon attached to the second tubular member, the inflatable balloon being in fluid communication with the connecting tube. The inflatable balloon is for insertion to the patient's urinary bladder, the balloon for locating the second tubular member substantially within the patient's prostatic urethra such that the connecting tube is held by the patient's sphincter.

Preferably, the connecting tube extends through the walls of the first and second tubular members.

The wall of the second tubular member may include a chamber in fluid communication with the connecting tube and the inflatable balloon.

Preferably, the connecting tube extends beyond the first tubular member so as to enable the connection thereof to an external inflating element.

According to further features in preferred embodiments of the invention described below, the catheter further includes a guiding element, including: (a) a substantially elongated tubular member having a hollow, the elongated tubular member having a closed end for insertion through the patient's urethra and an open end for connection to an external inflating element; (b) an inflatable balloon attached to the elongated tubular member, the inflatable balloon being in fluid communication with the hollow of the tubular member. The guiding element is for insertion through the first and second tubular members of the catheter so as to inflate the inflatable balloon of the guiding element against the walls thereof, thereby effectively fixing the catheter to the guiding element. Preferably, the inflatable balloon of the guiding element is substantially elongated and thin in cross section.

BRIEF DESCRIPTION OF THE DRAWINGS

The invention is herein described, by way of example only, with reference to the accompanying drawings, wherein:

FIG. 1a is a schematic longitudinal section of an internal catheter according to the present invention, wherein the locating balloon is inflated.

FIG. 1b is a schematic longitudinal section of an internal catheter according to the present invention, wherein the locating balloon is deflated;

FIG. 2 is a cross sectional view taken along line A—A in FIG. 1b;

FIG. 3 is a schematic longitudinal section of a guiding element according to the present invention;

FIG. 4 is a schematic longitudinal section of the guiding element illustrated in FIG. 3 while received within the internal catheter, wherein the locating balloon is inflated;

FIG. 5 is a cross sectional view taken along line B—B in FIG. 4; and

FIG. 6 is a schematic longitudinal section of the guiding element illustrated in FIG. 3 while received within the internal catheter, wherein the locating balloon is deflated.

DESCRIPTION OF THE PREFERRED EMBODIMENTS

The present invention is of an internal catheter for introduction into a patient's obstructed prostatic urethra so as to enable effective drainage of fluids and tissue particles through the obstructed urethra.

The principles and operation of apparatus and method according to the present invention may be better understood with reference to the drawings and the accompanying description.

Referring now to the drawings, FIGS. 1a, 1b and 2 illustrate an internal catheter according to the present invention. As shown, internal catheter 1 includes first and second tubular members, 2 and 4, interconnected by means of a connecting tube 6, the connecting tube for inflating a balloon 20 attached to tubular member 4.

As shown in the figures, connecting tube 6 preferably extends through the entire length of walls 8 of tubular member 2 and through a portion of the length of wall 10 of tubular member 4, such that the proximal end 6a of connecting tube 6 is embedded within wall 10 and the distal end 6b of connecting tube 6 is connected to an external connector 18.

Connector 18 is connectable to an injector for injecting fluid into connecting tube 6 so as to inflate balloon 20. Connector 18 preferably includes a valve or a tap (not shown) for controlling the flow of fluid into and out of connecting tube 6.

Wall 10 of tubular member 4 preferably includes a chamber 13 in fluid communication with connecting tube 6. An aperture 14 located on wall 10 provides fluid communication between chamber 13 and balloon 20. Balloon 20 is preferably attached to the external surface of wall 10 and encloses a segment thereof.

When the catheter is introduced to the patient's urethra, balloon 20 is inserted to the patient's urinary bladder in a deflated form. Balloon 20 is then inflated so as to temporarily anchor the catheter at a required position such that the portion 4a of tubular member 4 is located at the prostatic urethra, segment 6c of tubular connection 6 which connects tubular members 2 and 4 is held by the patient's sphincter, tubular member 2 is located at the patient's urethra distally to the sphincter, and the portion 6d of tubular connection 6 extends through the length of the patient's urethra. Connector 18 is located externally to the patient body.

As shown in the figures, tubular members 2 and 4 are preferably circular in cross section and feature substantially circular openings 15a, 15b, 16a and 16b, for allowing effective drainage of fluids and tissue particles. Alternatively, tubular members 2 and 4 may be cut at an angle so that openings 15 a and 15b feature a substantially elliptical shape.

Referring now to FIG. 3, according to the present invention there is provided a guiding element 3 for introducing catheter 1 to the patient's body. As shown in the figure, guiding element 3 preferably includes an elongated tubular member 30 having a proximal end 32 for insertion to the patient's urethra and a distal end 33 for connection to an external connector 39. Proximal end 32 preferably features a rounded shape for facilitating the insertion of the catheter through the patient's urethra. Distal end 33 is preferably open and circular in cross section for allowing connecting thereof to connector 39. Tubular member 30 is preferably made of a semi-rigid material.

Attached to tubular member 30 is an inflatable balloon 38, the balloon being in fluid communication with the hollow 34 of tubular member 38 via apertures 36 located along the length of wall 35 of tubular member 30. Preferably, inflatable balloon 38 is attached to the external surface of wall 35 and encloses a substantial portion of tubular member 30. The length of balloon 38 preferably substantially equals the distance between opening 16a of tubular member 4 and opening 15b of tubular member 2. Balloon 38 may extend along a limited portion of tubular member 30. Preferably, balloon 38 is substantially thin in cross section.

Connector 39 is connectable to an injector for injecting fluid into the hollow 34 of tubular member 30. Connector 39 preferably includes a valve or a tap (not shown) for controlling the flow of fluid into and out of hollow 34 of tubular member 30.

FIGS. 4–6 illustrates the usage of a guiding element according to the present invention for the introduction of catheter 1 to the patient's body.

Referring to FIG. 6, guiding element 3 is inserted into tubular members 2 and 4 while balloon 38 of guiding element 3 is deflated. Balloon 38 is then inflated by injecting fluid such as water or air into tubular member 30 by means of an injector connected to connector 39 (not shown) so as to substantially engage balloon 38 with the walls 8 and 10 of tubular members 2 and 4. Balloon 38 is inflated to such an extent so as to press the walls of balloon 38 against walls 8 and 10, thereby substantially fixing tubular members 2 and 4 to the balloon.

The assembly shown in FIG. 6 is then inserted into the patient's urethra so as to locate balloon 20 of catheter 3 within the patient's urinary bladder. Balloon 20 is then inflated by injecting fluid into connecting tube 6 by means of an injector connected to connector 18 (not shown) so as to temporarily anchor balloon 20 within the patient's urinary bladder, thereby appropriately positioning portion 4a of tubular member 4 within the patient's prostatic urethra such that portion 6c of connecting tube 6 is held by the patient's sphincter.

Following the positioning of the internal catheter within the patient's urethra, balloon 38 of guiding element 3 is deflated by pumping the fluid out of the balloon and tubular member 30 by means of the injector connected to connector 39. Guiding element 3 is then extracted from within the catheter and removed from the patient's body.

The positioning of tubular member 2 at one side of the sphincter and tubular member 4 at the other side of the sphincter effectively anchors the catheter in place. Therefore, balloon 20 may be only used as a locating balloon rather than a permanent anchoring balloon. Accordingly, following the extraction of guiding element 3 balloon 20 is preferably deflated by pumping the fluid out of the balloon by means of the injector connected to connector 18.

Portion 6d of connecting tube 6 may then be cut so as to hide the end of the connecting tube within the patient's urethra, thereby minimizing the risk of contamination and providing maximal comfort to the patient. Alternatively, portion 6d of connecting tube 6 may be cut so as to remain externally to the body, thereby enabling facile extraction of the catheter.

Alternatively, the step of using an injector for deflating balloon 20 is omitted and balloon 20 is deflated by cutting portion 6d of connecting tube 6.

While the invention has been described with respect to a limited number of embodiments, it will be appreciated that many variations, modifications and other applications of the invention may be made.

What is claimed is:

1. A catheter for insertion into a patient's urethra, comprising:
    (a) first and second tubular members having such a diameter for enabling drainage of physiological fluids therethrough, each of said first and second tubular members having a wall of a specific thickness, said first and second tubular members being interconnected by a connecting tube of substantially smaller diameter; and
    (b) a first inflatable balloon attached to said second tubular member, said first inflatable balloon being in fluid communication with said connecting tube, and thereby inflatable via said connecting tube; wherein,
        (i) said first inflatable balloon serves for insertion into the patient's urinary bladder, said balloon is positioned on said second tubular member and is inflatable to dimensions and shape, such that by inserting said first inflatable balloon to the patient's urinary bladder, inflating said first inflatable balloon, and pulling the catheter so as to position said balloon against the bladder, said second tubular member engages substantially the entire length of the patient's prosthetic urethra and extends into the bladder; and
        (ii) a portion of said connecting tube interconnecting said first and second tubular members has a length, such that when said second tubular member is positioned to engage substantially the entire length of the patient's prosthetic urethra and to extend into the bladder, said connecting tube engages substantially the entire length of the patient's sphincter, such that said first tubular member is located in the patient's urethra distally to the patient's sphincter, so as to allow drainage of fluid from the patient's bladder, through said second tubular member, through said patient's sphincter, through said first tubular member and through the patient's urethra out of the patient's body.

2. The catheter of claim 1, wherein said connecting tube extends through said walls of said first and second tubular members.

3. The catheter of claim 1, wherein said wall of said second tubular member includes a chamber in fluid communication with said connecting tube and said first inflatable balloon.

4. The catheter of claim 1, wherein said connecting tube extends beyond said first tubular member so as to enable the connection thereof to an external inflating element.

5. The catheter of claim 1, further comprising a guiding element, said guiding element including:

(a) a substantially elongated tubular member having a hollow extending along its length, said elongated tubular member having a closed end for insertion through the patient's urethra and an open end for connection to an external inflating element; and (b) a second inflatable balloon attached to said elongated tubular member, said second inflatable balloon being in fluid communication with said hollow of said tubular member via apertures being located along a length of a wall of said elongated tubular member, said guiding element being dimensioned for insertion through said first and second tubular members, such that when said second inflatable balloon is inflated said catheter is fixed to said guiding element.

6. The catheter of claim 5, wherein said second inflatable balloon is substantially elongated.

7. The catheter of claim 5, wherein said second inflatable balloon is substantially thin in cross section.

* * * * *

(12) EX PARTE REEXAMINATION CERTIFICATE (6027th)
United States Patent
Eshel et al.

(10) Number: US 5,916,195 C1
(45) Certificate Issued: Dec. 4, 2007

(54) INTERNAL CATHETER

(75) Inventors: Uzi Eshel, Herzelia (IL); Jacob Lazarovitz, Hod Hasharon (IL)

(73) Assignee: Argomed Ltd., Herzelia (IL)

Reexamination Request:
No. 90/005,756, Jun. 20, 2000

Reexamination Certificate for:
Patent No.: 5,916,195
Issued: Jun. 29, 1999
Appl. No.: 09/018,664
Filed: Feb. 4, 1998

(51) Int. Cl.
*A61M 25/06* (2006.01)
*A61M 25/00* (2006.01)
*A61M 25/10* (2006.01)
*A61F 2/00* (2006.01)

(52) U.S. Cl. .................... 604/96.01; 604/264
(58) Field of Classification Search ............ 604/96.01, 604/264, 271
See application file for complete search history.

(56) References Cited

U.S. PATENT DOCUMENTS

| | | | |
|---|---|---|---|
| 2,693,191 A | 11/1954 | Raiche | 128/349 |
| 3,045,677 A | 7/1962 | Wallace | 128/349 |
| 3,625,793 A | 12/1971 | Sheridan et al. | 156/229 |
| 3,811,450 A | 5/1974 | Lord | 128/349 R |
| 3,825,013 A | 7/1974 | Craven | 128/349 |
| 3,938,529 A | 2/1976 | Gibbons | 128/349 |
| 4,019,515 A | 4/1977 | Kornblum | 128/246 |
| 4,137,922 A | 2/1979 | Leininger et al. | 128/344 |
| 4,183,102 A | 1/1980 | Guiset | 3/1.4 |
| 4,407,271 A | 10/1983 | Schiff | 128/1 |
| 4,474,569 A | 10/1984 | Newkirk | 604/8 |
| 4,498,473 A | 2/1985 | Gereg | 128/207.15 |
| 4,555,242 A | 11/1985 | Saudagar | 604/96 |
| 4,610,660 A | 9/1986 | Rosenberg | 604/49 |
| 4,627,837 A | 12/1986 | Gonzalo | 604/101 |
| 4,655,746 A | 4/1987 | Daniels et al. | 604/53 |
| 4,671,795 A | 6/1987 | Mulchin | 604/281 |
| 4,686,985 A | 8/1987 | Lottick | 128/344 |
| 4,693,704 A | 9/1987 | Ogita | 604/55 |
| 4,710,169 A | 12/1987 | Christopher | 604/104 |
| 4,713,058 A | 12/1987 | Sachse | 604/165 |
| 4,762,129 A | 8/1988 | Bonzel | 128/344 |

(Continued)

FOREIGN PATENT DOCUMENTS

| | | |
|---|---|---|
| DE | 19540919 A1 | 7/1997 |
| EP | 0341988 B1 | 11/1989 |
| EP | 0733379 A1 | 9/1996 |
| EP | 0790041 A2 | 8/1997 |
| FR | WO9602210 A1 | 1/1996 |
| WO | WO92/04934 | 2/1992 |
| WO | WO92/18199 | 10/1992 |
| WO | WO93/04727 | 3/1993 |
| WO | WO 96/02210 A1 | 1/1996 |

*Primary Examiner*—Cris Rodriguez

(57) ABSTRACT

A catheter for insertion into a patient's urethra is provided, comprising: (a) first and second tubular members having such a diameter for enabling drainage of physiological fluids therethrough, the first and second tubular members being interconnected by means of a connecting tube of substantially smaller diameter; (b) an inflatable balloon attached to the second tubular member, the inflatable balloon being in fluid communication with the connecting tube. The inflatable balloon is inserted to the patient's urinary bladder so as to locate the second tubular member substantially within the patient's prostatic urethra such that the connecting tube is held by the patient's sphincter. Further according to the present invention there is provided a guiding element for insertion through the catheter, including: (a) a substantially elongated tubular member having a hollow, the elongated tubular member having a closed end for insertion through the patient's urethra and an open end for connection to an external inflating element; (b) an inflatable balloon attached to the elongated tubular member, the inflatable balloon being in fluid communication with the hollow of the tubular element, the inflatable balloon for inflation against the catheter so as to effectively fix the guiding element to the catheter.

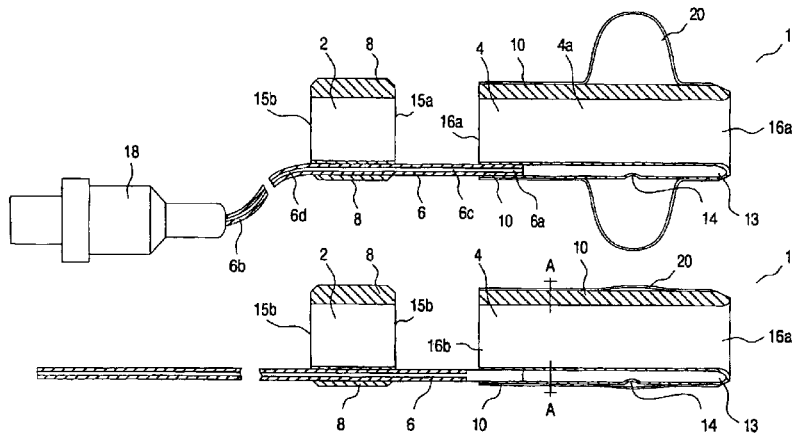

U.S. PATENT DOCUMENTS

| | | | |
|---|---|---|---|
| 4,762,130 A | 8/1988 | Fogarty et al. | 128/348.1 |
| 4,793,351 A | 12/1988 | Landman et al. | 128/344 |
| 4,819,751 A | 4/1989 | Shimada et al. | 128/344 |
| 4,823,812 A | 4/1989 | Eshel et al. | 128/804 |
| 4,878,901 A | 11/1989 | Sachse | 604/174 |
| 4,900,314 A | 2/1990 | Quackenbush | 604/282 |
| 4,909,785 A | 3/1990 | Burton | 604/54 |
| 4,931,037 A | 6/1990 | Wetterman | 604/8 |
| 4,932,938 A | 6/1990 | Goldberg et al. | 604/96 |
| 4,932,956 A | 6/1990 | Reddy et al. | 606/192 |
| 4,946,449 A | 8/1990 | Davis, Jr. | 604/256 |
| 4,950,227 A | 8/1990 | Savin et al. | 604/8 |
| 4,955,859 A | 9/1990 | Zilber | 604/8 |
| 4,973,301 A | 11/1990 | Nissenkorn | 604/8 |
| 4,979,948 A | 12/1990 | Geddes et al. | 606/33 |
| 4,983,167 A | 1/1991 | Sahota | 606/194 |
| 4,994,066 A | 2/1991 | Voss | 606/108 |
| 4,995,872 A | 2/1991 | Ferrara | 604/280 |
| 5,007,437 A | 4/1991 | Sterzer | 428/786 |
| 5,007,898 A | 4/1991 | Rosenbluth et al. | 604/54 |
| 5,019,075 A | 5/1991 | Spears et al. | 606/7 |
| 5,041,092 A | 8/1991 | Barwick | 604/104 |
| 5,059,169 A | 10/1991 | Zilber | 604/8 |
| 5,098,374 A | 3/1992 | Othel-Jacobsen et al. | 604/8 |
| 5,098,379 A | 3/1992 | Conway | 604/51 |
| 5,112,306 A | 5/1992 | Burton et al. | 604/101 |
| 5,151,100 A | 9/1992 | Abele et al. | 606/28 |
| 5,163,906 A | 11/1992 | Ahmadi | 604/101 |
| 5,176,626 A | 1/1993 | Soehendra | 604/8 |
| 5,188,596 A | 2/1993 | Condon et al. | 604/101 |
| 5,192,289 A | 3/1993 | Jessen | 606/155 |
| 5,269,802 A | 12/1993 | Garber | 606/191 |
| 5,286,259 A | 2/1994 | Ganguly et al. | 604/96 |
| 5,295,959 A | 3/1994 | Gurbel et al. | 604/96 |
| 5,306,241 A | 4/1994 | Samples | 604/54 |
| 5,312,430 A | 5/1994 | Rosenbluth | 606/192 |
| 5,314,443 A | 5/1994 | Rudnick | 606/192 |
| 5,322,501 A | 6/1994 | Mahmud-Durrani | 604/8 |
| 5,338,302 A | 8/1994 | Hasson | 604/105 |
| 5,372,600 A | 12/1994 | Beyar et al. | 606/108 |
| 5,383,856 A | 1/1995 | Bersin | 604/101 |
| 5,391,196 A | 2/1995 | Devonec | 607/96 |
| 5,419,763 A | 5/1995 | Hildebrand | 604/54 |
| 5,439,446 A | 8/1995 | Barry | 604/96 |
| 5,451,218 A | 9/1995 | Moore | 604/317 |
| 5,453,090 A | 9/1995 | Martinez et al. | 604/53 |
| 5,478,349 A | 12/1995 | Nicholas | 606/198 |
| 5,484,411 A | 1/1996 | Inderbitzen et al. | 604/96 |
| 5,499,994 A | 3/1996 | Tihon et al. | 606/192 |
| 5,514,092 A | 5/1996 | Forman | 604/101 |
| 5,514,178 A | 5/1996 | Torchio | 623/12 |
| 5,518,498 A | 5/1996 | Lindenberg et al. | 600/30 |
| 5,527,336 A | 6/1996 | Rosenbluth | 606/192 |
| 5,545,132 A | 8/1996 | Fagan et al. | 604/96 |
| 5,549,559 A | 8/1996 | Eshel | 604/113 |
| 5,588,965 A | 12/1996 | Burton | 604/101 |
| 5,593,412 A | 1/1997 | Martinez et al. | 606/108 |
| 5,609,583 A | 3/1997 | Hakki et al. | 604/282 |
| 5,669,930 A | 9/1997 | Igarashi | 606/191 |
| 5,685,847 A | 11/1997 | Barry | 604/96 |
| 5,718,686 A | 2/1998 | Davis | 604/101 |
| 5,725,547 A | 3/1998 | Chuter | 606/194 |
| 5,752,971 A | 5/1998 | Rosenbluth | 606/192 |
| 5,766,209 A | 6/1998 | Devonec | 604/8 |
| 5,785,641 A | 7/1998 | Davis | 600/30 |
| 5,836,951 A | 11/1998 | Rosenbluth | 606/108 |
| 5,876,417 A | 3/1999 | Devonec et al. | 606/192 |
| 5,876,517 A | 3/1999 | Jeannier | 148/264 |

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *